United States Patent
Walen

(10) Patent No.: US 10,206,702 B2
(45) Date of Patent: Feb. 19, 2019

(54) RONGEUR WITH CUTTING IMPLEMENT THAT IS SELECTIVELY DRIVEN BY A MOTOR SO THE CUTTING IMPLEMENT PERFORMS EITHER POWER ASSISTED OR MANUAL CUTTING OF TISSUE

(71) Applicant: Stryker Corporation, Kalamazoo, MI (US)

(72) Inventor: James G. Walen, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 140 days.

(21) Appl. No.: 15/185,199

(22) Filed: Jun. 17, 2016

(65) Prior Publication Data
US 2016/0296247 A1 Oct. 13, 2016

Related U.S. Application Data

(63) Continuation of application No. PCT/US2014/071187, filed on Dec. 18, 2014.

(60) Provisional application No. 61/919,006, filed on Dec. 20, 2013.

(51) Int. Cl.
*A61B 17/32* (2006.01)
*A61B 17/16* (2006.01)

(52) U.S. Cl.
CPC .... *A61B 17/32002* (2013.01); *A61B 17/1611* (2013.01); *A61B 2017/320028* (2013.01); *A61B 2017/320032* (2013.01)

(58) Field of Classification Search
CPC ............ A61B 17/1604; A61B 17/1606; A61B 17/1608; A61B 17/1611; A61B 2017/320024; A61B 17/32053; A61B 17/320783
See application file for complete search history.

(56) References Cited

U.S. PATENT DOCUMENTS

| | | | |
|---|---|---|---|
| 4,586,497 A | 5/1986 | Dapra et al. |
| 4,678,459 A | 7/1987 | Onik et al. |
| 4,777,948 A | 10/1988 | Wright |
| 5,061,269 A | 10/1991 | Muller |

(Continued)

FOREIGN PATENT DOCUMENTS

WO 2004049956 A3 9/2004

OTHER PUBLICATIONS

International Search Report for Application No. PCT/US2014/071187 dated May 27, 2015, 5 pages.

(Continued)

*Primary Examiner* — Thomas McEvoy
(74) *Attorney, Agent, or Firm* — Howard & Howard Attorneys PLLC

(57) ABSTRACT

A rongeur (34) for driving a cutting unit (240) that includes an outer (240) tube and a cutting implement (302) able to both rotate in move longitudinally in the outer tube The rongeur includes a body (36) to which a rotating spindle (102) for actuating the cutting implement is mounted. The spindle is designed to allow the inner tube to while, rotating move longitudinally relative to the spindle. A mechanism (150, 180) attached to the body selectively displaces the drive inner tube so the distal end of the cutting implement can be advanced towards and retracted away from the distal end of the outer tube.

18 Claims, 18 Drawing Sheets

(56) References Cited

U.S. PATENT DOCUMENTS

| | | | |
|---|---|---|---|
| 5,290,303 | A | 3/1994 | Pingleton et al. |
| 5,569,284 | A | 10/1996 | Young et al. |
| 6,689,050 | B1 | 2/2004 | Beutter et al. |
| 7,422,582 | B2 | 9/2008 | Malackowski et al. |
| 7,691,107 | B2 | 4/2010 | Schneiter |
| 7,922,723 | B2 | 4/2011 | Michelson |
| 8,230,867 | B2 | 7/2012 | Mark |
| 8,241,290 | B2 | 8/2012 | Michelson |
| 9,095,366 | B2 | 8/2015 | Sullivan et al. |
| 9,339,288 | B2 | 5/2016 | Sullivan et al. |
| 2003/0163134 | A1* | 8/2003 | Riedel ................ A61B 17/162 606/79 |
| 2004/0059363 | A1 | 3/2004 | Alvarez et al. |
| 2004/0102783 | A1 | 5/2004 | Sutterlin et al. |
| 2008/0221606 | A1 | 9/2008 | Faulhaber et al. |
| 2010/0121365 | A1 | 5/2010 | O'Sullivan et al. |
| 2010/0160823 | A1 | 6/2010 | Parihar et al. |
| 2010/0179578 | A1 | 7/2010 | Tannoury et al. |
| 2013/0023882 | A1 | 1/2013 | Fabro et al. |
| 2013/0310866 | A1 | 11/2013 | Belagali |

OTHER PUBLICATIONS

Aesculap, Inc., "Aesculap Neurosurgery—Pneumatic Kerrison", 2008, pp. 1-11.

* cited by examiner

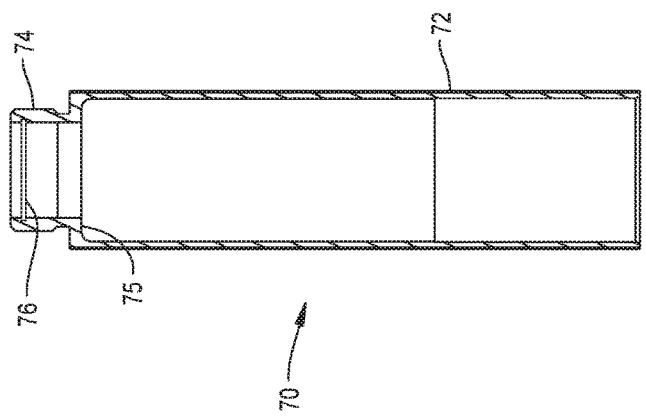
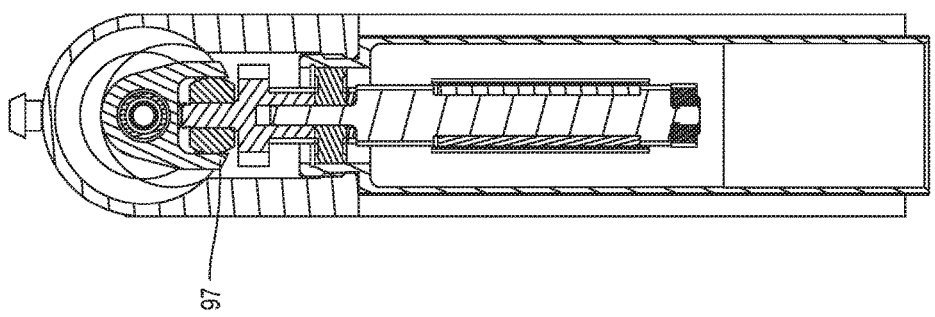

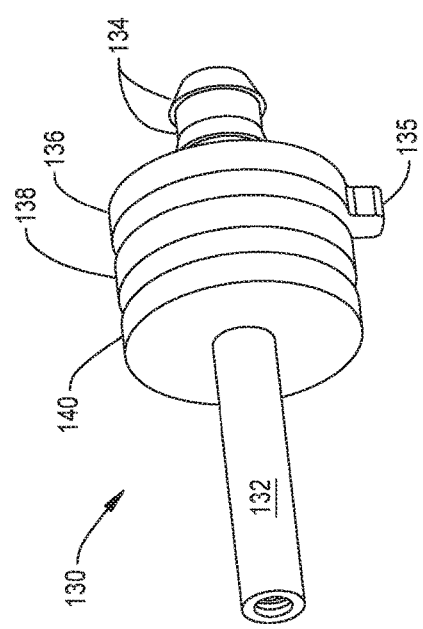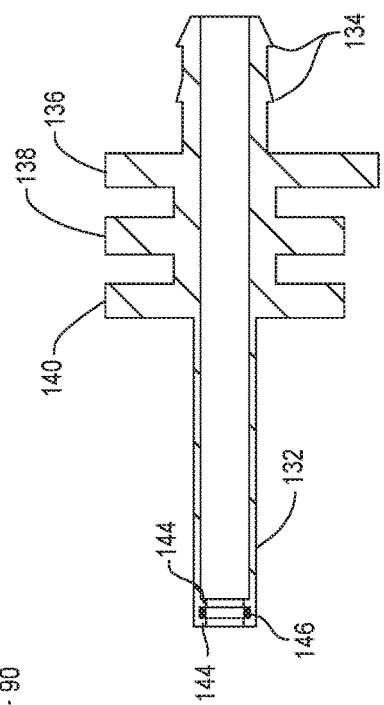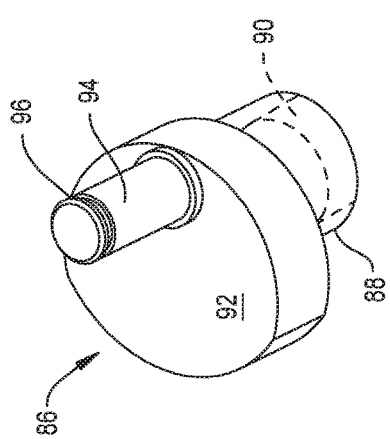

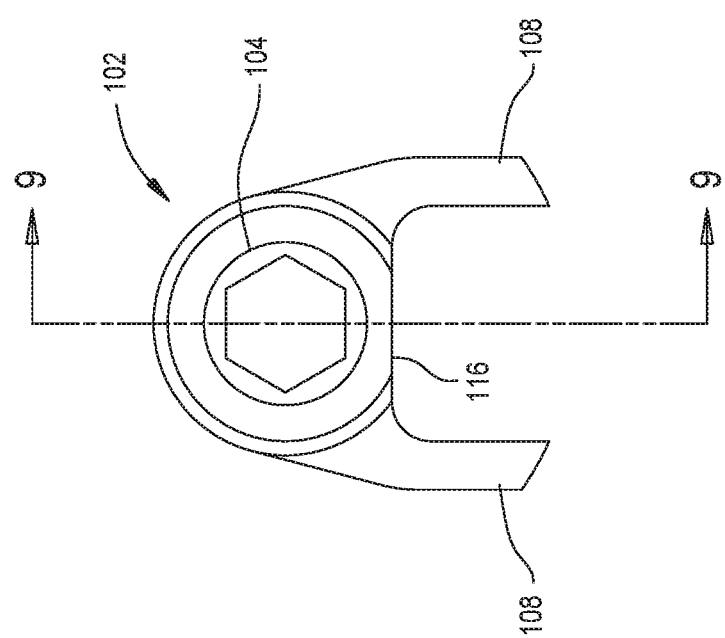

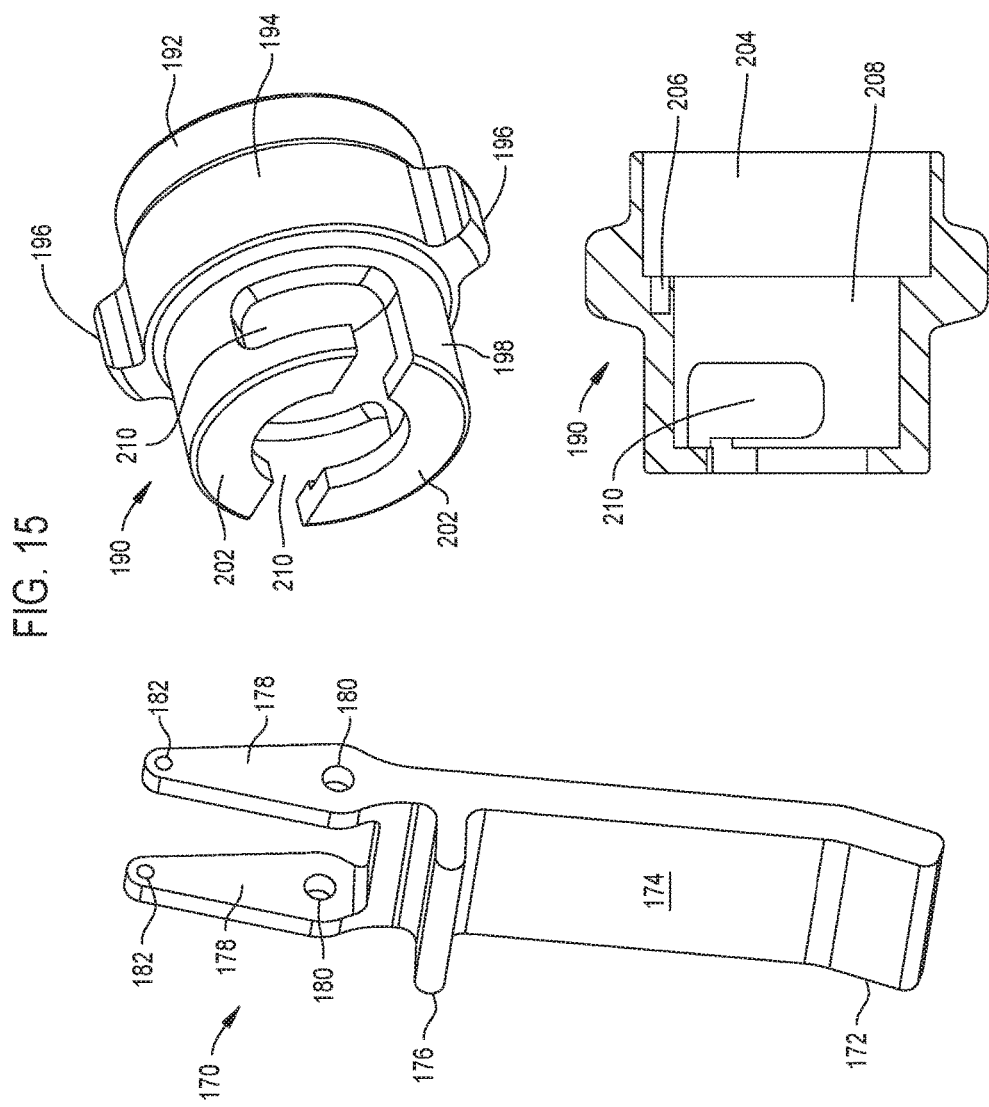

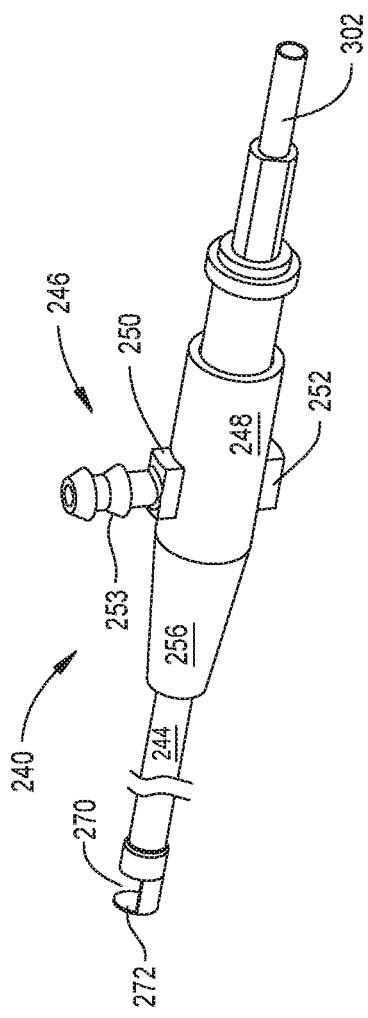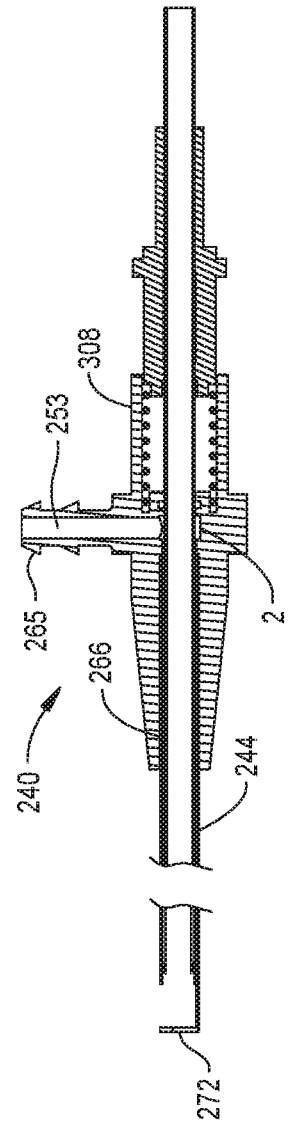
FIG. 18
FIG. 19

RONGEUR WITH CUTTING IMPLEMENT THAT IS SELECTIVELY DRIVEN BY A MOTOR SO THE CUTTING IMPLEMENT PERFORMS EITHER POWER ASSISTED OR MANUAL CUTTING OF TISSUE

FIELD OF THE INVENTION

This invention relates generally to a powered rongeur. The powered rongeur of this invention has a motor that power assistance for cutting the tissue to which the rongeur is applied. The rongeur of this invention is further designed so the practitioner can manually cut the tissue to which the rongeur is applied.

BACKGROUND OF THE INVENTION

A rongeur is a surgical tool used to remove a small volume of tissue. One type of rongeur is a Kerrison rongeur. At its most basic, a Kerrison rongeur consists of a static outer tube in which an inner tube, called a cutting tube, is slidably disposed. A plate is disposed over the distal end of the outer tube. The outer tube is also formed with a side opening immediately proximal to the plate. The distal end of the cutting tube is open. The cutting tube is formed so as to have either a cutting edge or cutting teeth that extend circumferentially around the open end of the tube. A rongeur is used to remove tissue by positioning the tubes so that the tissue to be removed protrudes into the outer tube through the side opening. The cutting tube is brought forward to excise from trapped tissue from the adjacent tissue. A rongeur has proven to be a useful surgical tool because the only tissue that is subject to removal is the tissue within the outer tube. This substantially reduces the likelihood that nearby tissue not intended for removal inadvertently comes into contact with the teeth or cutting edge of the cutting tube.

It is known to further provided a rongeurs with a suction connections to the proximal end of the cutting tube. This arrangement allows a suction to be drawn through the cutting tube. This suction draws away the tissue as the tissue is separated from the adjacent tissue. This eliminates the need for the practitioner to, after each bit of tissue is cut, remove the rongeur from the site at which it is applied, remove the cut tissue and then reposition the rongeurs so a new section of tissue can be removed.

One type of rongeur is a rongeur that is purely manually actuated. To use this type of rongeur, the practitioner manually reciprocates the cutting tube back and forth to cut the tissue targeted for removal. Typically the rongeur includes a lever arm that is pivotally connected to the inner tube. The practitioner repetitively moves this lever arm back and forth so as to induce a like movement of against the tissue targeted for removal. A disadvantage of this type of rongeur is that the practitioner is required to use muscles power to perform the whole of the cutting process. Having to repetitive use muscles to both hold the rongeur steady and reciprocate the cutting tube against tissue that is resistant to cutting can fatigue the hand and fore arm. This is especially true if the rongeurs is being used repeatedly to remove a number of different sections of tissue.

To remedy this problem, powered rongeurs have been proposed. This type of rongeur includes a handpiece to which a motor is slidably mounted. The cutting tube extends from the motor. The outer tube is static relative to the handpiece. A linkage system allows the practitioner to move the motor relative to the handpiece. This results in the like movement of the distal end of the cutting tube relative to the outer tube. When tissue is to be removed using this type of rongeur, the motor and cutting tube are advanced distally forward so the cutting edge/teeth is/are forced against the tissue to be removed. The motor is actuated. The rotation or oscillation of the motor results in the like movement of the cutting edge/teeth against the tissue. This movement, in combination with the force placed on the teeth by the practitioner results in the severing of the target tissue.

An advantage of the above device is that it eliminates the need for the practitioner to have to repetitively employ muscle power to force the cutting of the target tissue by the rongeur. However, a limitation of this device is that it only allows the motor system to perform the cutting of the tissue to which it is applied. There are number of procedures for which the practitioner may want to switch between using manual force and the supplied powered force to cut the tissue against which the rongeurs is applied. For example, when the rongeur is spaced from tissue it is important not be cut, the practitioner may decide that, to speed the procedure and minimize muscle fatigue, it is useful to use the supplied force, the motor force, to cut the tissue. Then, as the rongeur approaches tissue that it is important not be cut, the practitioner may want to rely solely on manual force to perform the cutting. This manual force while slower than the powered force, allows would provide the practitioner more control than would be obtained by rely on mechanical force to overcome the resistance of the tissue to being cut.

Another reason a practitioner may want to interleave the use of manual and mechanized forces to cut the tissue is that the resistance to which the practitioner is exposed by using manual force to cut the tissue can provide feedback regarding the condition of the tissue and/or the cutting process.

Also, a further disadvantage of known motorized rongeurs is that the practitioner is required to use muscle force to press both the cutting tube and associated motor against the target tissue. During the severing process it is desirable to only apply a select amount of force longitudinally against the tissue being removed. With the described type of device, the practitioner is required to apply manual force that holds both the cutting tube and the attached motor against the tissue. This may make it difficult for the practitioner to precisely control the extent to which the cutting tube is pressed against the tissue. For example, if the rongeur is directed downwardly, gravity may apply a force against the motor that also urges the cutting tube against the tissue. In this situation, the practitioner must adjust the force he/she applies to compensate for the added gravitational force that is also urging the cutting tube against the tissue. Alternatively, if the rongeurs is directed upwardly, gravity may work to force the cutting tube away from the tissue against which the tube is to be applied. This can require the practitioner to use apply more force than he/she might normally use in order to press the tube against the tissue to be removed.

SUMMARY OF THE INVENTION

This invention is related to a new and useful powered rongeur. The rongeur of this invention includes a motor that can provide a substantial amount of the force that is applied against the target tissue to perform the cutting process. The rongeur of this invention also includes a manually actuated linkage that moves the cutting implement so that the implement, and only the cutting implement, can be manually extended towards and retracted away from the target tissue The rongeur of this invention includes a handpiece. A motor is statically mounted in the handpiece. The motor actuates an output spindle. Also disposed in the handpiece is a drive collar. The drive collar is located adjacent the spindle. The drive collar is able to move proximally and distally within the handpiece. A control member attached to the handpiece that is manipulated by the practitioner allows the practitioner to set the longitudinal position of the drive collar.

The rongeur of this invention also includes a cutting unit. The cutting unit includes an outer tube and a cutting implement. The cutting implement is shaped to move both longitudinally and rotationally within the outer tube. The handpiece and outer tube are provided with complementary features that facilitate the static mounting of the outer tube to the handpiece. The spindle and the cutting implement are provided with complementary features that couple the cutting implement to the spindle so that cutting implement both rotates in unison with the spindle and moves longitudinally relative to the spindle. This invention is further constructed so the drive collar abuts the cutting implement.

A practitioner using the rongeur of this invention positions the rongeur so the tissue to be excised is disposed between the outer tube and the cutting implement. By manipulating the control member the practitioner advances the drive collar distally forward. This results in a like forward motion of the cutting implement. The tissue to be excised is thus pressed between the two tubes. If the practitioner wants to using power assisted force, motor force, to cut the tissue, the handpiece motor is actuated. This results in the movement of the cutting implement against the tissue in action that results in the cutting of the tissue.

Alternatively, the practitioner can, using the rongeur of this invention, manually cut tissue. To perform this task, the practitioner using the control member, manually reciprocates the cutting implement against the tissue. This action results in the cutting implement chopping the tissue to separate the tissue from the adjacent tissue. Thus, this invention can be used to either manual excise tissue or employ mechanized force to perform this process.

A further feature of the rongeur of this invention is that when the practitioner advances the cutting implement, the only components that are advanced are the drive collar and the cutting implement. The motor remains static relative to the handpiece during the process of advancing or retracting the cutting implement.

In many versions of the invention, the cutting implement is a cutting tube. In still other versions of the invention, the cutting implement is a bur.

BRIEF DESCRIPTION OF THE DRAWINGS

The above and further features and benefits of this invention are understood from the following Detailed Description taken in conjunction with the accompanying drawings in which

FIG. 3 is a cross sectional view of the rongeur taken along line 3-3 of FIG. 2.

FIG. 5 is a cross sectional view of the grip of the handpiece

FIG. 6 is a perspective view of the eccentric internal to the handpiece;

FIG. 10 is a plan view of the distally directed end of the spindle;

FIG. 11 is a perspective view of the end cap of the handpiece;

FIG. 11A is a cross sectional view of the cap of FIG. 11;

FIG. 14 is a perspective view of the cutting trigger of the handpiece;

FIG. 15 is a perspective view of the lock ring of the handpiece;

FIG. 16 is a cross sectional view of the lock ring of FIG. 15;

FIG. 18 is a perspective view of the cutting unit of the rongeur of this invention;

DETAILED DESCRIPTION

I. Overview

Figure 1:
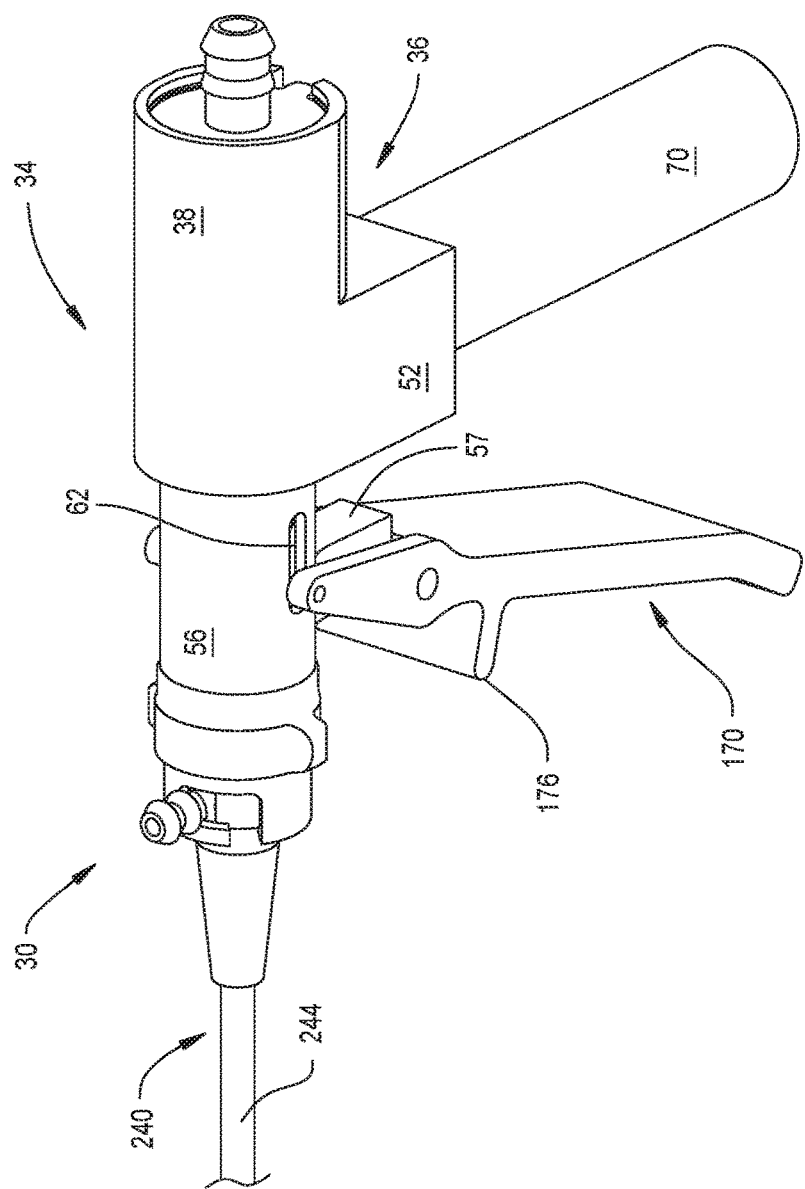
FIG. 1 is a perspective view of the rongeur of this invention.
Figure 19A:
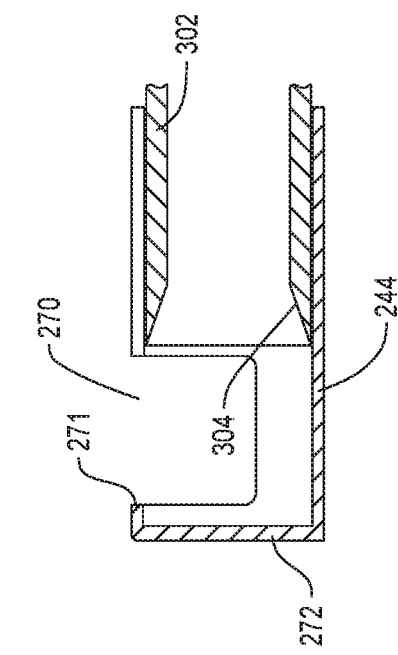
FIG. 19 is a cross sectional view of the proximal portion of the cutting unit of FIG. 18.

As seen in FIG. 1, rongeur 30 of this invention includes a handpiece 34 to which a cutting unit 240 is removably attached. Cutting unit 240 includes an outer tube 244 that is removably statically mounted to the handpiece 34. A cutting implement 302 (FIG. 19), is disposed inside outer tube 244. The depicted cutting implement is a cutting tube 302 and is referred to as such throughout this Detailed Description. Cutting tube 302 is able to both rotate in and move longitudinally in the outer tube 302. A motor 80 (FIG. 2) is disposed inside the handpiece 34. The cutting tube 302 is connected to the motor 80 to engage in at least some rotation upon actuation of the motor. Cutting tube 302 is also slidably mounted to the handpiece 34 so that the cutting implement is able to move relative to the motor 80. Cutting tube 302 is able to engage in this movement even while the tube 302 is actuated by the motor 80.

A cutter trigger 170 is moveably mounted to the handpiece 34. Cutter trigger 170 is the control member that the practitioner manually actuates to set the position of the cutting tube 302.

II. Handpiece

Figure 4:
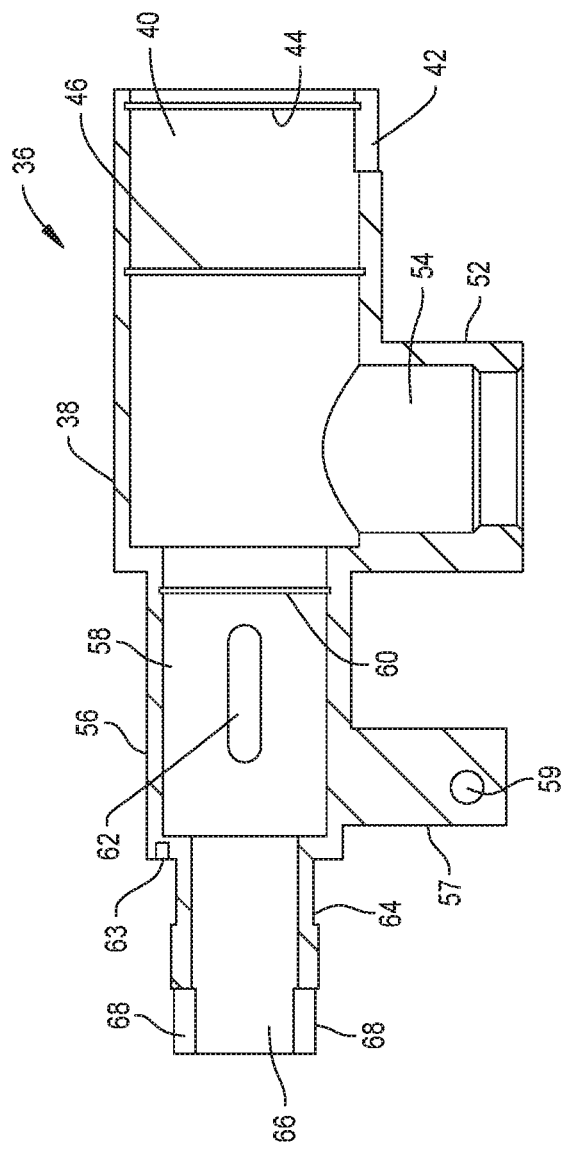
FIG. 4 is a cross sectional view of the barrel, head and nose of the handpiece.
Figure 7:
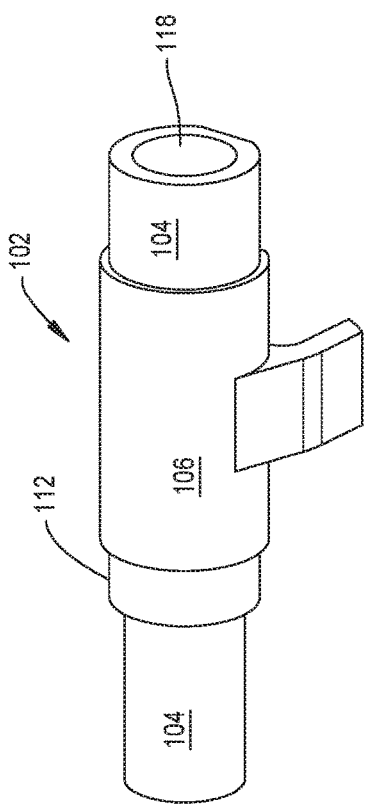
FIG. 7 is a perspective view of the spindle of the handpiece wherein the proximal end of the spindle is visible.
Figure 9:
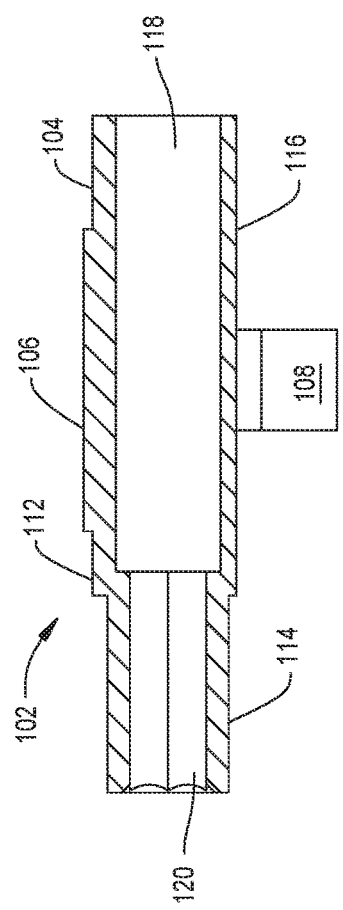
FIG. 9 is a cross sectional view of the spindle.
Figure 8:
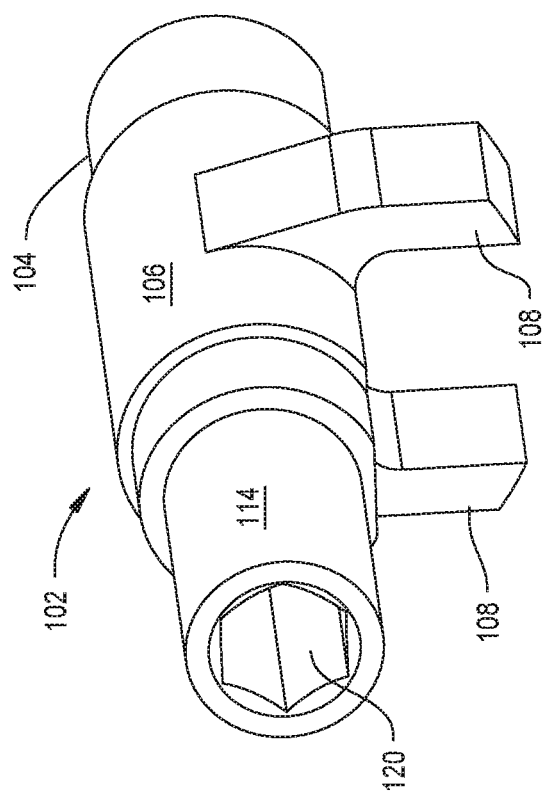
FIG. 8 is a perspective view of the spindle of FIG. 7 wherein the distal end of the spindle is visible.

The depicted handpiece 34, as seen in FIGS. 1 and 4, includes a body 36 that is generally pistol shaped. Specifically, the handpiece has a barrel 38 from which a grip 70 extends downwardly. Barrel 38 has a proximal section, not identified, that is generally cylindrical in shape. ("Proximal" is understood to mean towards the practitioner holding the rongeur 30; away from the surgical site to which the rongeur is applied. "Distal" is understood to mean away from the practitioner holding the rongeur 30; towards the surgical site to which the rongeur is applied.) Handpiece body 36 is further formed so that a rectangular boss 52 projects downwardly from the distal section of the barrel 38. Distally forward of the barrel 36, handpiece body 34 is formed to have a head 56 that is coaxial with the barrel. Head 56 is has an outer diameter that is smaller than the outer diameter of barrel 36. A nose 64 projects distally forward of the front end of head 56. Nose 64 is generally cylindrical and coaxial with head 56. The nose 64 has an outer diameter less than the outer diameter of head 56. Body 36 is further formed so as to have a closed end bore 63 that extends inwardly from the step that defines the transition between head 56 and nose 64.

In the depicted version of the invention, body barrel 38, head 56 and nose 64 are formed as a single piece unit. Integral with this unit is a block 57. Block 57 is extends outwardly from head 56. Grip 70 is a separate component secured to barrel boss 40.

Handpiece barrel 38, head 56 and nose 64 are formed with a number of contiguous bores and openings. Specifically, a bore 40 extends from the proximal end of the barrel 38 through the barrel to head 56. Barrel 38 is further formed so as have a notch 42 that extends distally forward a short distance from the proximal end of the barrel. The barrel 38 is further formed to have two grooves 44 and 46 that extend circumferentially around and outwardly from the inner wall of the barrel 38 that defines bore 40. Groove 44 is located a short distance distally forward of the proximal end of the barrel 38. Groove 44 intersects notch 42. Groove 46 is located rearward of the location from which boss 52 extends outwardly from the barrel 38. Boss 52 is formed to have a bore 54 that opens into barrel bore 40. Boss bore 54 has a longitudinal axis that is perpendicular to the longitudinal axis of barrel bore 40.

Barrel bore 40 opens into an adjacent bore 58 formed in head 56. A short distance forward of the barrel-head interface the head 56 is formed with a groove 60. Groove 60 extends circumferentially around and radially outwardly from the inner wall of the head 56 that defines bore 58. Forward of groove 60, the head head 56 is formed to have two oval shaped slots 62. Slots 62 are located on the opposed sides of the head 56, the portions of the head 56 perpendicular to the section of the head from which block 57 extends. Slots 62 open into head bore 58. The proximal end of head bore 58 opens into a bore 66 that extends axially through nose 64. The open end distal end of nose bore 66 forms the open distal end of the handpiece body 36. Handpiece body 36 is further formed so that two slots 68 extend proximally rearward from the distal end of nose 64. Slots 68 open into bore 66. Slots 68 are diametrically opposed to each other relative to the longitudinal axis of through bore 66.

Block 57 is formed to have a through bore, bore 59. Bore 59 extends side to side through the block 57. The longitudinal axis of bore 57 is perpendicular to the longitudinal axis through head bore 58.

In the depicted version of the invention, grip 70, as now described by FIG. 5, is shown as having a tubularly shaped base 72. A head 74 extends outwardly from the top end of base 72. Head 74 has a diameter less than that of base 72. The outer surface of head 74 is formed with threading, (not illustrated). More specifically, grip head 74 is shaped and threaded to seat in and engage with the threading integral with bore 59 internal to block 57.

A circular step 75 projects inwardly from an inner wall of the grip base 72. Step 75 defines a through opening, not identified, between the void space internal to the grip base 72 below the step and the portion of the head 72 located above the step 75. Grip 70 is further formed to have an annular groove 76 that extends circumferentially around the inner cylindrical wall of head 76. Groove 76 is located above step 74.

Figure 2:
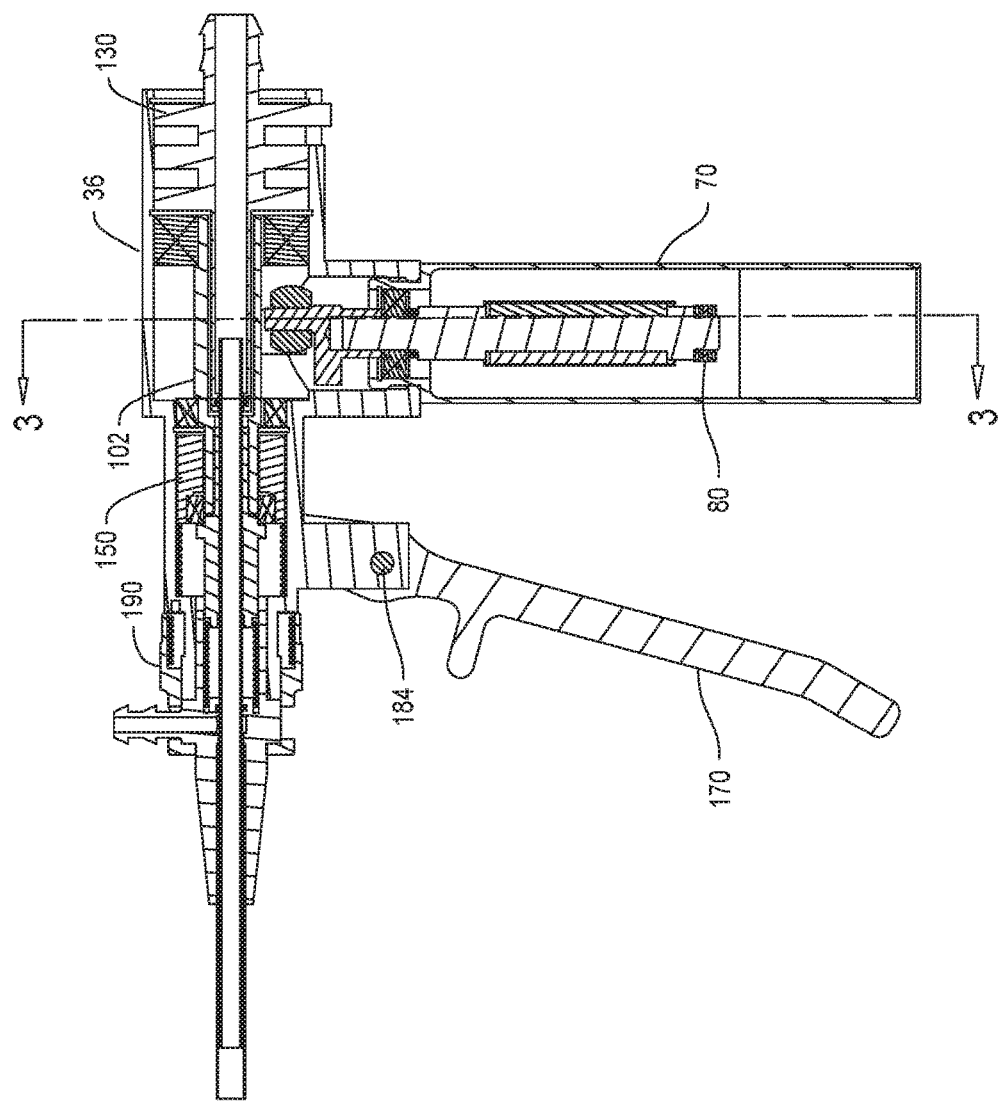
FIG. 2 is a cross sectional view of the rongeur of FIG. 1.

Motor 80 is disposed in grip 70. In some versions of the invention motor 80 is a brushless DC motor. The structure of the motor is not part of the present invention. In the depicted version of the invention, the motor, as seen in FIGS. 2B and 3, is shown as having an outer diameter less than the diameter of the wall internal to grip 70 that defines the void space internal to the grip base 72. Motor 80 is an electrical driven motor. How the motor is held in grip is neither illustrated nor part of the present invention. The motor rotor has an exposed head 82 that projects through the center opening defined by step 74. A bearing assembly 85 rotatably holds hold rotor head 82 to the inner wall of grip head 72. A snap ring (not illustrated) seated in groove 76 extends over the outer race of bearing assembly 86 to hold the bearing assembly in grip 70. When handpiece 34 is assembled, motor rotor head 82 extends above grip 70 into boss bore 54.

An eccentric 86, best seen in FIGS. 2B and 6, is mounted to the exposed end of motor rotor head 82 so as to rotate with head 82. Eccentric 86 is a single piece component formed to have a cylindrical base 88. A closed end bore 90 (shown in phantom) extends through base 88. Bore 90 is coaxial with base 88 and shaped to receive motor rotor head 82. A circular head 92 is located above the base 88. Head 92 and extends radially outwardly beyond the base 88. Head 92 has a height less than that of base 88. A drive pin 94 projects upwardly from the circular top surface of head 92. Drive pin 94 is in the form of solid cylinder. Eccentric 86 is formed so that the longitudinal axis of the drive pin 94 is radially spaced from the longitudinal axis of base 88. A groove 96 extends circumferentially around the outer surface of drive pin 94 immediately below the top of the pin.

When handpiece 34 is assembled, motor rotor head 82 is press fit or otherwise securely fitted in eccentric bore 90. Eccentric 86 thus rotates with the rotation of the motor rotor. The components of handpiece 34 are further arranged so that eccentric drive pin 94 is disposed within the section of body bore 40 immediately above boss bore 54.

The eccentric 86 drives a spindle 102 rotatably disposed in the handpiece barrel 38 and head 56. As best seen in FIGS. 7-10, the drive spindle 102 is a single piece unit. The drive spindle 102 is formed to have a number of sections that, in cross section, are at least partially circular in shape and that are centered around a common longitudinal axis, (axis not identified. The proximalmost of these sections is a tail 104. Tail 104 is generally cylindrical in shape. Distally forward of tail 104, the drive spindle 102 is shaped to have a torso 106 that is also generally cylindrical in shape. Torso 106 has an outer diameter that is greater than the outer diameter of the tail 104.

Two legs 108 project outwardly from spindle torso 106. Each leg 108 has a base that is portion of the leg that extends from the torso (bases not identified). The bases are generally triangular in shape. Each leg 108 has a extension (extensions not identified) that extends outwardly from the base to form the free end of the leg. Legs 108 are further formed so that the opposed inner surfaces of the leg extensions are parallel to each other.

Distally forward of the torso 106, the drive spindle 102 is formed to have two additional sections that are centered around the longitudinal axis of the spindle. Specifically, a generally cylindrical neck 112 is located immediately forward of the torso 106. Neck 112 has an outer diameter approximately equal to that of tail; 104. Forward of neck 112, the drive spindle 102 has a cylindrical head 114. Head 114 has a diameter less than that of the neck 112.

Spindle tail 104, torso 106 and neck 112 are described as being approximately cylindrical. This is because the spindle 102 is formed to have a flat 116 that extends longitudinally along the spindle. Flat 116 intersects the outer surfaces of the spindle tail 104, torso 106 and neck 112. Drive spindle 102 is formed so the flat 116 is within the section of the torso 106 between the legs 108.

Two contiguous bores 118 and 120 form a through channel between the proximal and distal ends of the drive spindle. Bore 118 extends forward from the proximal end of tail 104, through the tail and substantially through torso 106. The spindle 106 is formed so bore 118 is, in cross section, circular in shape. Bore 118 opens into bore 120. Bore 120 starts a short distance proximal to the transition between the neck 112 and head 114 of the spindle and extends completely through the head 114. In cross section, in planes perpendicular to the longitudinal axis of the spindle 102, bore 120 is non-circular. In the illustrated version of the invention, bore 120 is hexagonal in cross section. Not identified are the faces of drive spindle head 114 that define the outer perimeter of bore 120.

Handpiece 34 is assembled so that the spindle tail 104 and torso 106 are located in the distal portion of bore 40. Spindle neck 112 and head 114 are located in the proximal portion of bore 58. A bearing assembly 122, identified in FIG. 2B, rotatably holds the spindle 102 in bore 40. The outer race of bearing assembly 122 (outer race not identified) is press fit or slip fit over spindle tail 104. A snap ring (not illustrated) is seated in handpiece barrel groove 46. This snap ring extends into bore 40 and is located adjacent the proximally directed face of the outer race of bearing assembly 122 (outer race not illustrated). This snap ring prevents rearward movement of the bearing assembly and, by extension, the drive spindle. A bearing assembly 124, identified in FIG. 2B rotatably holds the drive spindle 102 in bore 58. The inner race of the bearing assembly 124 is press or snap fit over spindle neck 112. A snap ring (not illustrated) is seated in handpiece groove 60. This snap ring projects into bore 58 so as to be located adjacent the distally directed face of the outer race of bearing assembly 124. This snap ring prevents the forward movement of the bearing assembly 124 and, by extension, drive spindle 102.

When the drive spindle 102 is mounted in the handpiece body, the opposed legs 108 of the spindle are located on the opposed sides of the eccentric drive pin 94. A bearing assembly 97 is press or snap fit over the drive pin 94. The opposed parallel inner surfaces of drive spindle legs 108 are disposed against the opposed sides of the outer surface of the outer race of bearing assembly 96.

From the above, it should be understood that the proximal end of the drive spindle 102 is disposed in handpiece bore 40 so as to be located forward of the proximal end of the bore 40. A cap 130, now described with respect to FIGS. 11 and 11A, is disposed in the section of bore 40 located proximal to the drive spindle 104. The cap 130 is formed from a single piece of material such as PEEK or aluminum. Cap 130 is shaped to have an elongated tube like stem 132. The proximal end of the stem 132 has barbs 134 that extend circumferentially around the stem. Barbs 134 are spaced apart from each other. The features of the cap 130 are dimensioned so that the proximal end of stem 132, including barbs 134, function as fitting to which a suction line (not illustrated) can be attached.

Cap 130 is further formed to have three parallel discs 136, 138 and 140 that are located to distal to barbs 134. Discs Ribs 136, 138 and 140 are circular in shape and project radially outwardly from stem 132. The discs 136, 138 and 140 have an outer diameter that is snug fit relative to the diameter of handpiece bore 40. The cap 130 is further formed so that the discs 136-140 are spaced apart from each other along the longitudinal axis of stem 132. While the discs are generally identical in shape, the proximalmost disc, disc 136 includes a feature not present on discs 138 and 140. Specifically, disc 136 is formed with an outwardly extending tab 135. Tab 135 is dimensioned to snuggly fit in notch 42 formed in handpiece barrel 38.

Figure 12:
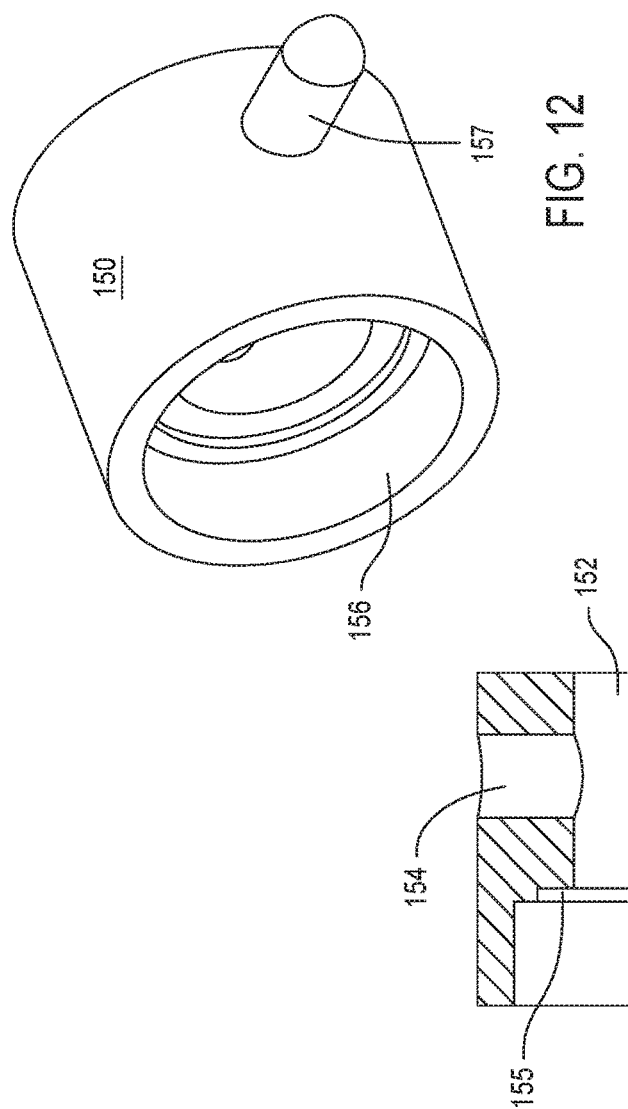
FIG. 12 is a perspective view of the drive collar of the handpiece.

The cap 130 is formed so that stem 132 extends distally forward from discs 136-140. Given the tubular shape of stem 132 it should be appreciated that the stem 132 has an axially extending lumen 142 that extends from between the proximal and distal ends of the stem. Cap 130 is further formed so two ribs 144 project inwardly from the inner surface of the stem 132 that defines lumen 142. A first rib 144 is located adjacent the distal end of the stem 132. A second rib 144 is spaced a small distance proximally rearward of the distal rib 144. An O-ring 146, seen only in FIGS. 2B and 12, is disposed in the annular space in lumen 142 between the ribs 144. O-ring 146 projects inwardly of the ribs 144.

Upon assembly of handpiece 34, the cap 130 is positioned so that proximal disc 136 is located immediately forward of groove 44 internal to the handpiece barrel 38. The proximal section of stem 132 projects proximally rearward from the barrel. Discs 136-140 are disposed within the barrel 38 in the space between grooves 44 and 46. The portion of stem 132 that extends forward of disc 140 extends through distal section of barrel bore 40 and into the space subtended by bearing assembly 124. Thus the distal portion of stem 124 is disposed in bore 118 internal to the drive spindle 102.

A snap ring (not illustrated) is seated in groove 44. This snap ring projects into barrel bore 40 so as to prevent the rearward movement of cap 130 out of the bore.

Figure 13:
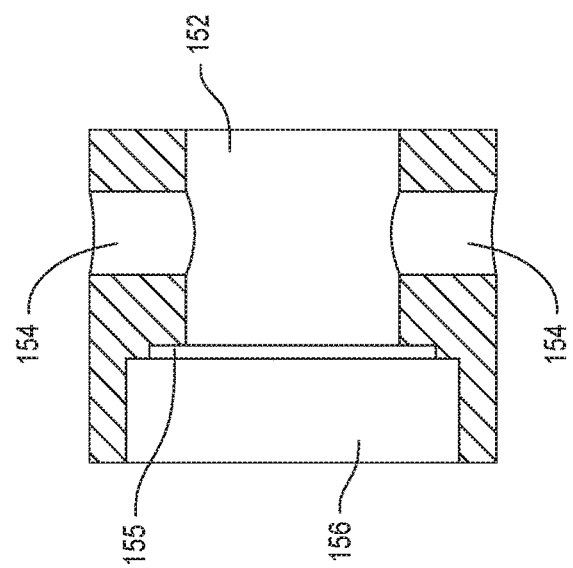
FIG. 13 is a cross sectional view of the drive collar of FIG. 12.

A drive collar 150 is slidably disposed in handpiece head bore 58. The drive collar 150 is disposed over the head 114 of the drive spindle 102. From FIGS. 12 and 13 it can be seen that the drive collar 150 is a single piece component that is generally cylindrically shaped. Drive collar 150 is dimensioned to slide freely in handpiece bore 58. Three bores 152, 155 and 156 form a contiguous through opening between the opposed proximal and distal ends of the drive collar 152. The proximal bore, bore 152 has a diameter that is slightly larger than the outer diameter of spindle head 114. Bore 152 opens up into distal bore 155. Bore 155 opens into a longer length bore, bore 156. Bore 156 has a diameter larger than the diameter of bore 155. The drive collar 152 is formed to have two axially aligned holes 154. The axis on which holes 156 are centered extends through bore 152 and is perpendicular to the proximal-to-distal longitudinal axis through the drive collar 150. A pin 157, one only seen in FIG. 12, is press fit in each collar hole 156.

Figure 2A:
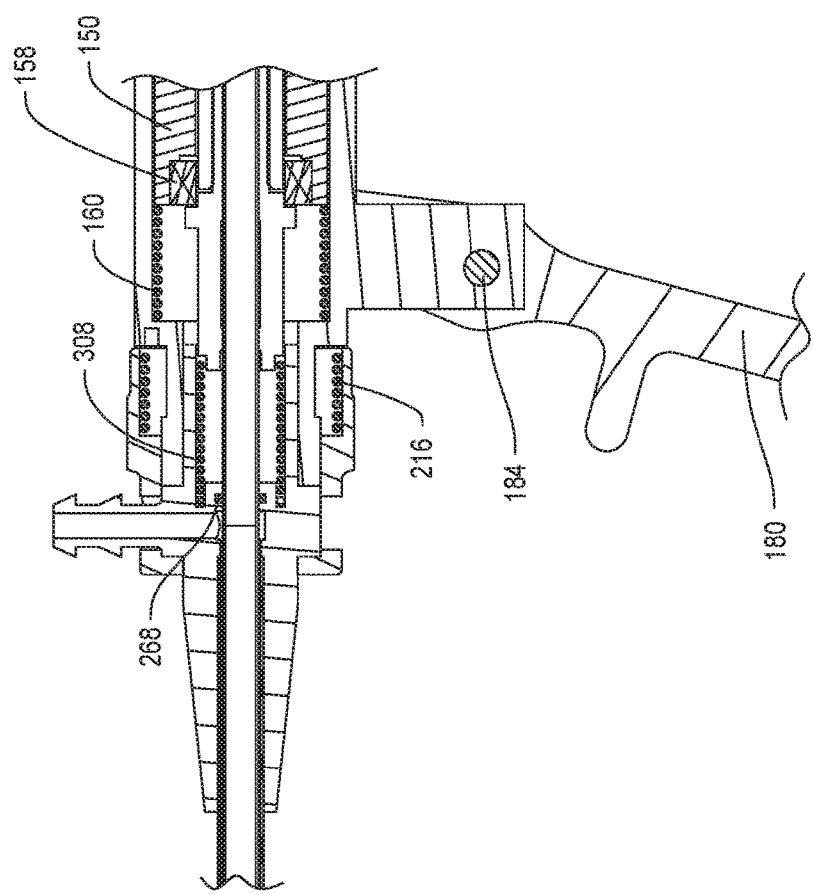
FIG. 2A is an enlarged cross sectional view of how the cutting unit seated in the handpiece of the rongeur.
Figure 2B:
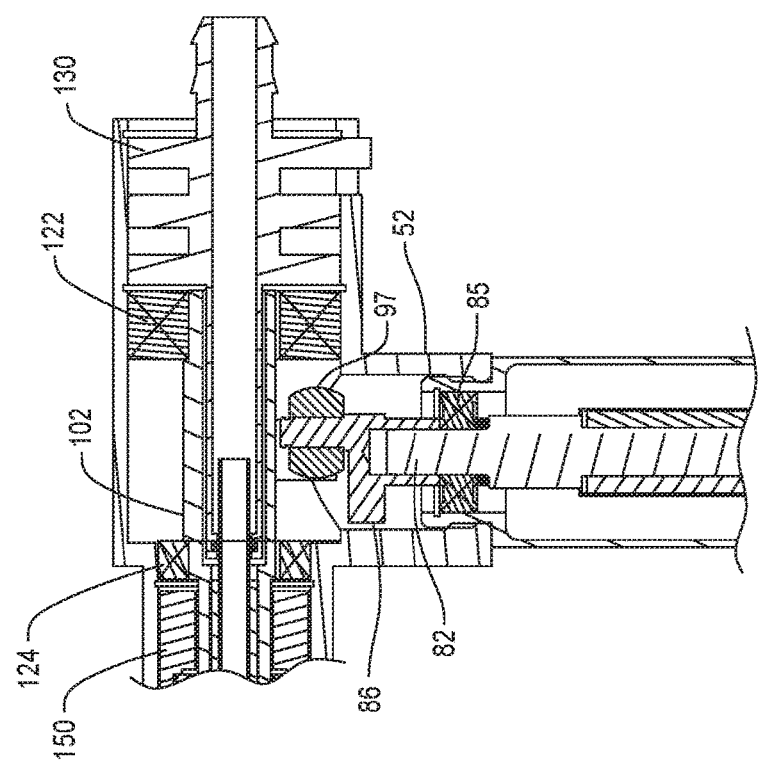
FIG. 2B is an enlarged cross sectional view of the proximal end of handpiece.

A bearing assembly 158, identified in FIG. 2A, is disposed in collar bore 156. Bearing assembly 158 has an inner race, (not depicted) with a diameter that allows the race to slide over spindle head 114. The inner race of bearing assembly 158 faces drive collar bore 155.

Drive collar 150 and bearing assembly 158 are collectively dimensioned to slide freely in handpiece bore 58 and over spindle head 114. Each pin 157 extends through and is able to move in the adjacent slot 62 formed in the handpiece head 56. Owing to the dimensioning of the components forming the handpiece 34, the drive collar 150 is able to move in the handpiece bore 58 to a position forward of the drive spindle 102. A helical spring 160, seen only in FIG. 2A, extents forward of drive collar 150 in handpiece bore 58. The distal end of the spring 160 is disposed against the annular step internal the handpiece that defines the transition from bore 58 to bore 66. Spring 160 exerts a force on drive collar 150 that, in the absence of another force, holds the collar in its proximal position within handpiece bore 58.

Cutter trigger 170, now described by reference to FIG. 14, is a single piece component. The trigger 170 includes a rectangular shaped beam 174 that is the main body of the trigger. A foot 172 angles away from the base of the beam so as to extend downwardly and distally forward. Adjacent the top of the beam 174, trigger 170 is formed with a tab 176. Tab 176 projects perpendicularly forward from the beam 174.

Two parallel arms 178 extend upwardly from the top of beam 174. Each arm 178 lies in a plane that is perpendicular to the plane in which beam 174 is oriented. Arms 178 are spaced apart from each other so as to fit on the opposed sides of handpiece head 56. Each arm 178 is generally in the shape of a triangle with a rounded apex. Immediately above beam 174, each arm 178 is formed with a through opening 180. Through openings 180 are coaxially aligned. Below the apex of each arm 178, trigger 170 is formed to have a through opening 182. The through openings 182 are coaxially aligned.

A pin 184, seen in cross section in FIGS. 2 and 2A, extends between trigger openings 180 and through bore 59 internal to handpiece block 57. The pin 184 pivotally connects trigger 170 to the rest of the handpiece 34. A linkage, not illustrated, connects each trigger arm 178 to the adjacent collar pin 157. Typically the linkage is connected to trigger arm 178 by a pin that is seated in arm opening 182. In some versions of the invention, the linkage assembly is a single bar. In these versions of the invention arm opening 182, instead of being circular, is oval in shape. This allows the attached bar to both pivot and move relative to the arm 178.

A lock ring 190, seen best in FIGS. 15 and 16, is rotatably mounted over handpiece nose 64. Lock ring 190 is a single piece component formed to have a ring shaped base 192. A trunk 194, also generally ring shaped, extends forward from the base 192. Trunk 194 has an outer diameter greater than that of base 192. Two diametrically opposed tabs 196 extend radially outwardly from opposed sides of trunk 194. Forward of the trunk 194, the lock ring has a generally cylindrical head 198. The lock ring 190 is formed so that head 198 has an outer diameter less than that of base 192. Two arcuately shaped lips 202 extend inwardly from the outer surface of head 198. The outer surfaces of lips 202 form the distally directed face of the lock ring 190.

Lock ring 190 is formed so a bore 204 extends inwardly from the proximal end of base 192. Bore 204 has an outer diameter greater than that of handpiece nose 64. The distal end of bore 204 opens into a bore 208. Bore 208 has a diameter less than that of bore 204. Bore 208 extend forward so as to form a distal end opening into lock ring 190. At the distal end of the lock ring, 190, lips 202 project into the bore.

A small closed end bore 206 also extends distally forward from bore 204. Bore 206 extends forward from the annular step internal to the lock ring that defines the transition between bores 204 and 208.

The lock ring 190 is further formed so that head 198 has two diametrically opposed L-shaped slots 210. The short portion of each slot 210 extends proximally from the distal end of the head. Each slot 202 is thus the void space between the adjacent ends of lips 202. The long section of each slot 210 extends a short distance arcuately around the curved outer surface of the head.

Lock ring 190 is rotatably mounted to handpiece nose 64 through a means neither illustrated nor part of the present invention. The components forming handpiece 34 are formed so that inner wall of the lock ring 190 that defines the outer perimeter of bore 204 is spaced radially outwardly from the underlying section of nose 64.

Figure 17:
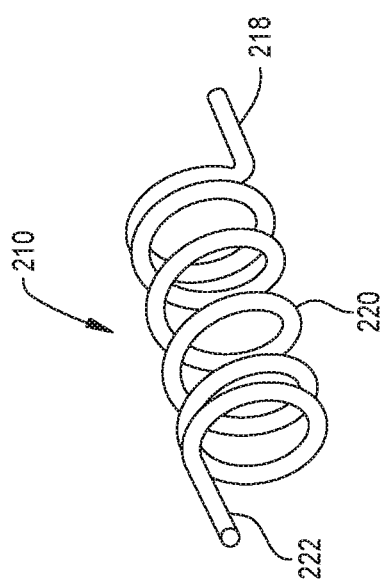
FIG. 17 is a perspective view of the torsion spring internal to the lock ring.

A torsion spring 216 is disposed in the annular gap between nose 64 and the adjacent bore 204-defining inner wall of the lock ring 190. The torsion spring 216, seen best in FIG. 17, has a center body 220 that comprise a set of helical turns. Two legs 218 and 222 extend outwardly from the opposed ends of the body 220. Legs 218 and 222 extend outwardly from the body 196 along axes that are parallel to the longitudinal axis through the center body 220. Leg 218 extends proximally. Leg 222 extends distally.

Handpiece 34 is assembled so that the center body 196 of spring 220 is the portion of the spring disposed around handpiece nose 64. Leg 218 seats in bore 63 formed in handpiece body 36. Leg 222 seats in lock ring bore 206. Collectively the handpiece is designed so that spring 220 normally holds the lock ring 190 in a rotational orientation around nose 64 so that portions of lock ring head 198 forward of the long sections of slots 210 extend over nose slots 68. Manual force is used to overcome the spring force and rotate the lock ring 190. More particularly, the lock ring can be rotated to an orientation in which the open distal ends of the lock ring slots 210 are in registration with nose slots 68.

III. Cutting Unit

Figure 20:
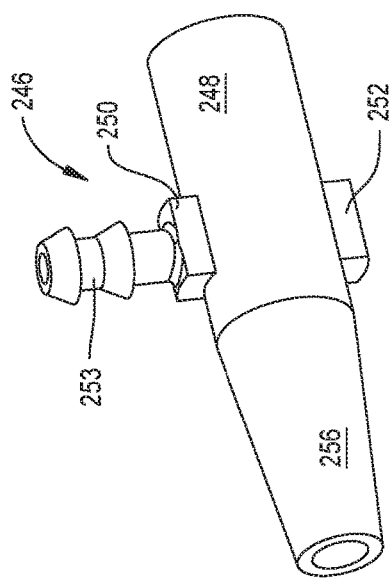
FIG. 20 is a perspective view of the outer hub of the cutting unit of FIG. 18.
Figure 21:
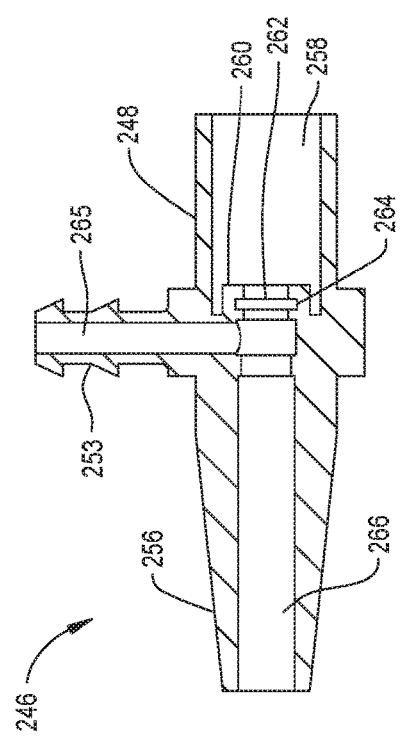
FIG. 21 is a cross sectional view of the outer hub of FIG. 20.

Cutting unit 240 of this invention, now generally described by reference to FIGS. 18 and 19, includes outer tube 244 and cutting tube 302. The outer tube 244 extends forward from an outer hub 246. The outer hub 246 now described by reference to FIGS. 20 and 21 is formed from a single piece of plastic. The outer hub 246 is shaped to have a cylindrical base 248. A nose 256 extends distally forward from base 248. Nose 256 has a tapered shape such that as the nose extends forward from base 248, the diameter of the nose decreases. Outer hub 246 is further shaped so that two rectangularly shaped ears 250 and 252 extend radially outwardly from base 248. The ears 250 and 252 are located closer to nose 256 than to the proximal end of the base 248. Ears 250 and 252 diametrically opposed to each other relative to the longitudinal axis through the hub 246. The ears 250 and 252 are dimensioned to seat in the slots 210 formed in the handpiece lock ring 210. A luer fitting or hose barb 253 extends outwardly from ear 250.

Outer hub 246 has a set of bores that form a lumen that extends axially between the opposed proximal and distal ends of the hub. A first one of the bores, bore 258, extends forward from proximal of the base 248. The outer hub 246 is further formed so that internal to the base 248 a cylindrical boss 260 extends proximally into the distal end of bore 258. The outer diameter of boss 260 is less than the diameter of bore 258. Thus there is a circular gap (not identified) in bore 258 around the outer perimeter of boss 260. A bore 262, that is contiguous with bore 258, extends through boss 260 and into hub nose 256. Bore 262 has an outer diameter that is less than the diameter of bore 258. The outer hub 246 is further formed so as to have a groove 264 that extend outwardly from cylindrical wall internal to boss 260 that defines the proximal end of bore 262. Not identified is where the lumen 265 of fitting 253 intersects and terminates in bore 262. The location where the fitting lumen 253 terminates in bore 262 is distally forward of groove 264. At this intersection, the diameter of bore 262 is slightly greater than the diameter of the bore 262 proximal and distal to this intersection. A bore 266 extends distally forward from bore 262 through hub nose 256 so as to form the distal end opening into outer hub 246. Bore 266 has a diameter that is greater than the diameter of bore 262 and less than the diameter of bore 258.

An O-ring 268, seen only in FIG. 2A, is disposed in groove 264. The O-ring 268 projects into bore 262.

The outer tube 244 itself is heat staked or otherwise secured in hub bore 266. The outer tube 244 extends distally forward from hub 246. The outer tube 244 is formed so that at the distal end of the tube there is a face plate 272. Spaced a short distance proximally away from the face plate 272, the outer tube 244 has a notch 270. Immediately proximal to the face plate 272, the outer tube has a notch 270. The distal end of notch 270 is defined by an arcuately shaped lip 271 that extends distally away from face plate 272.

Figure 22:
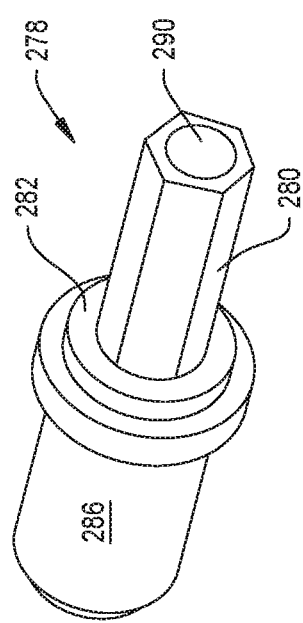
FIG. 22 is a perspective view of the inner hub of the cutting unit of FIG. 18.
Figure 23:
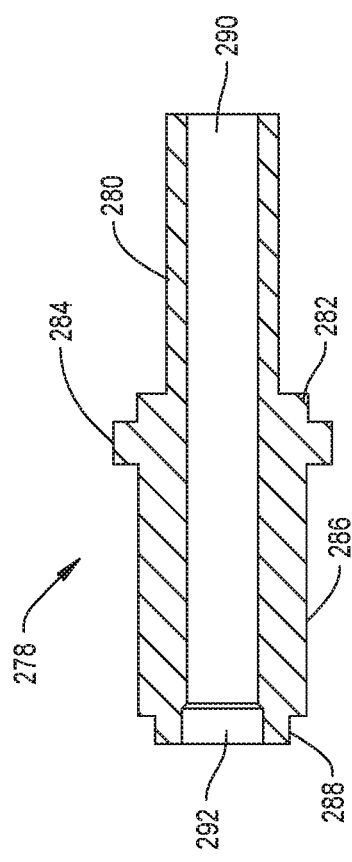
FIG. 23 is a cross sectional view of the inner hub of FIG. 21.

Cutting tube 302 is mounted to an inner hub 278 best seen in FIGS. 22 and 23. Inner hub 278 is formed from the same type of plastic from which outer hub 246 is formed. The inner hub is shaped to have a stem 280. Stem 280 has a non-circular shape such that the stem can closely slip fit in spindle bore 120. Thus, in the depicted version of the invention, stem 280 has a cross sectional shape that is hexagonal. Forward of stem 280, inner hub 278 has a circularly shaped bearing surface 282. Bearing surface 282 is located radially outwardly from stem 280. More particularly, the bearing surface is dimensioned to closely slip fit against the inner race of handpiece bearing assembly 158. Forward of bearing surface 282, the inner hub is formed to have a stop ring 284. The stop ring protrudes radially outwardly from bearing surface 282. In cross section, stop ring 284 is circular in shape.

The inner hub 278 has a head 286 that is located forward of the stop ring 284. Head 286 is generally cylindrical in shape and has an outer diameter less than that of the stop ring 284. Hub 278 is formed so that head 286 can slide within outer hub bore 258. A nose 288 that is significantly shorter in length that head 286, projects forward of the head 286. Nose 288 has an outer diameter less than that of head 286.

Inner hub 278 is further formed to have a bore 290 that extends from the proximal end of the hub. Bore 290 extends through substantial the entire length of the hub, terminating at a location slightly proximal to the transition between head 286 and nose 288. The bore 290 opens into a counterbore 292 that forms the open distal end opening into the inner hub 278. Counterbore 292 has an outer diameter greater than that of bore 290.

The cutting tube 302 itself is heat staked or otherwise secured in inner hub bore 290. Cutting tube 302 is secured to the inner hub 278 so that the proximal end of the tube 302 extends proximally rearward from hub stem 280. The distal end of the tube is open. Cutting tube 302 is formed so that the annular distal end of the tube has a beveled surface 304. From the inner wall of tube 302, beveled surface 304 (FIG. 19A) extends radially outwardly and distally forward. Beveled surface 304 defines a cutting edge located at the most distal end of the tube 302. While not illustrated, in some versions of the invention the distal end of cutting tube 302 may be formed to have teeth or serrations.

When cutting unit 240 is assembled, cutting tube 302 is slidably disposed inside outer hub 246 and outer tube 244. Within the outer hub 246, a spring 308, seen in FIGS. 2A and 19, is disposed over the cutting tube 302. More particularly the spring 308 is disposed in outer hub bore 258. The proximal end of spring 308 is disposed over inner hub nose 288. The distal end of spring 308 is disposed over outer hub boss 260. Spring 308 holds the inner hub 278 away from the outer hub boss 260. Further when the cutting unit 240 is assembled O-ring 268 bears against the section of the cutting tube 302 that extends through boss 260. The O-ring 268 thus forms a seal around the outer portion of the cutting tube 302 distal to the O-ring.

IV. Operation

Rongeur 30 of this invention is prepared for use by attaching the cutting unit 240 to the handpiece 34. This process starts with the rotating of lock ring 190 so that the distal portions of lock ring slots 210 go into registration with handpiece body slots 68. At this time, the lock ring 190 is in the load position. Once the lock ring is so oriented the cutting unit 240 can be inserted into the handpiece 34 so that the outer hub ears 250 and 252 each seat in a separate one of the handpiece body slots 68. The manual force used to rotate the lock ring 190 is released. Spring 216 rotates the lock ring back to the locked position. When the lock ring is in this state, the portions of the lock ring distal to the long arcuate sections of slots 210 are located forward of the outer hub ears 250 and 252. Lock ring 190 thus releasably prevents removal of the cutting unit 240.

When the cutting unit 240 is seated in the handpiece, stem 280 integral with the inner hub 278 seats in drive spindle bore 120. Owing to the force imposed by spring 308, inner hub 278 is urged proximally away from outer hub 246. The proximal movement of the inner hub 278 is limited by the abutment of hub stop ring 284 against the inner race of bearing assembly 158. Spring 160 holds the drive collar 150 in the proximal position within handpiece body bore 58.

The process of reading the handpiece for use also includes the attachment of a suction line (not illustrated) to the exposed portion of cap stem 132. A line for supplying irrigating fluid (not illustrated) is attached to outer hub fitting 253. Motor 80 is attached to a source of power. One source of power may be the power console that is the subject of the Inventor's Assignee's U.S. Pat. No. 7,422,582, the contents of which is explicitly incorporated herein by reference. This document describes how a practitioner can regulate a surgical power tool, by depressing the pedal of a footswitch assembly. Once the above steps are completed, rongeur 30 is considered readied for use. When the motor 80 is connected to a control console it is connected to the console by way of a cable not illustrated and not part of the present invention.

Use of rongeur 30 of this invention starts the same way use of a conventional rongeur is started. The distal end of the cutting unit is positioned so that the section of tissue to be removed extends through notch 270 at the distal end of the outer tube 244. The practitioner may actuate the motor 80 to perform assisted cutting of the tissue using the rongeur 30. To perform this type of cutting, the practitioner actuates the appropriate control member to cause the actuation of the motor 80. This results in eccentric pin 85 rotating bearing assembly 97 around a circle. Since drive spindle leg 108 are disposed against the opposed sides of bearing assembly 97, the movement of the bearing assembly oscillates the drive spindle 102 back and forth through an arc. Given that the inner surfaces of spindle that define bore 120 press against the inner hub stem 280, this motion is transferred to the cutting tube 302 to result in a like oscillation of the cutting tube 302.

To cut tissue, the practitioner is required to do more than oscillate the cutting tube 302. Simultaneously with the oscillation of the cutting tube the practitioner depresses trigger 170. The pivotal movement of trigger beam 170 is transferred to trigger arms 178 and the attached links to the drive collar 150. This force overcomes the force spring 160 imposes on the drive collar. The drive collar 58 and bearing assembly 158 advance distally forward through the handpiece body bore 58. During this translation motion of the drive collar and the bearing assembly, the inner race of the bearing assembly 158 pushes against stop ring 284 integral with inner hub 278. This force overcomes the force spring 308 imposes on the inner hub 278. The inner hub 278 and, by extension, the cutting tube 302 are advanced distally forward. During this motion it should be understood that at least a portion of the inner hub stem 280 remains disposed in the drive spindle bore 120. Thus even though the cutting tube 302 is being longitudinally advanced relative to the drive spindle 102, as long as the drive spindle is actuated, the cutting tube is simultaneously oscillated.

The cutting edge of the cutting tube 302 is thus simultaneously oscillated back and forth against the tissue to be cut while being pressed against the tissue. The application of these two forces simultaneous by the cutting tube 302 against the tissue is the power assisting cutting of the tissue by rongeur 30. It should further be understood that the tissue being cut is pressed between lip 271 of the outer tube 244 and the cutting edge of the cutting tube. Depending on the exact geometry of this lip 271 and the end of the cutting tube 302, (surface 304), a scissors like cutting action may cause the desired tissue separation.

Alternatively, the practitioner can rely solely on manual force to remove the tissue disposed in the outer tube 244. To so remove tissue, the practitioner pivots trigger 170 back and forth without simultaneously actuating the motor 80. This results in the cutting edge at the distal end of the cutting tube being repeatedly pressed against the tissue in the outer tube 244. This cutting action is enhanced by the fact that the tissue being cut is being sheared between outer tube lip 271 and the cutting edge of the cutting tube. The cutting tube 302 thus cuts the tissue in an action similar to that performed by conventional manually powered Kerrison rongeur.

During the manual cutting process, the act of reciprocating the trigger 170 back and forth is assisted by springs 160 and 308. This is because after the practitioner releases force holding the trigger beam 174 in its proximal position, springs 160 and 308 output a return force that returns the drive collar 150 and cutting tube 302 to their proximal positions.

During either tissue removal process, irrigating fluid may be flowed through fitting 253 and the annular gap between the inner surface of the outer tube 244 and the outer surface of the cutting tube 302 to the site at which the rongeur is provided. If this irrigating fluid is provided O-ring 268 prevents the fluid from flowing proximally through the cutting unit beyond fitting lumen 265.

When tissue is excised using rongeur 30, the suction source draws the tissue through the cutting tube 302, the cap stem 132 and the attached suction line to the collection canister (canister not illustrated and not part of this invention). The O-ring 146 provides a seal between the cap stem 132 and the cutting tube 302 that prevents a loss of suction where these two components interface.

Rongeur 30 of this invention thus provides the practitioner the option of performing either a power, motor, assisted cutting of tissue or the manual cutting of tissue. The practitioner can even switch between these two cutting modes in the same procedure and even without removing the rongeur from the site to which the rongeur is applied. Thus, if during one portion of a tissue removal process the practitioner finds it useful to perform power assisted tissue removal, by actuating the motor this type of process can be performed. Then, by simply deactivating the motor and reciprocating the cutting tube 302, the practitioner can at the same location engage in manually actuated removal of the tissue. Likewise the practitioner can similarly switch from a manual tissue removal process to the power assisted process.

Thus the practitioner can with a single portion of tissue disposed in the outer tube 244 partially cut the tissue using the power assisted process and then switch to cutting the tissue manually. Alternatively, the practitioner can initially perform the manual process to first define the section of tissue to be cut. Then once the cut is partially formed, the practitioner can complete the tissue removal using the motor assisted process.

It is a further feature of this invention that the power assisted tissue removal process, as implied by its name, power assisted. It is not a process wherein once initiated, the process runs independently of any force contribution by the practitioner. In order to perform the power assisted cutting, the practitioner must still manually supply the force needed to urge the cutting tube 302 against the tissue to be cut. This means that the practitioner obtains tactile feedback about the cutting process with respect to the resistance of the tissue to being cut and the position of the trigger. This latter feedback is an inferential indication of the distance between the end of the cutting tube and the adjacent surface of the outer tube face plate 272. The practitioner may find this feedback useful in determining the degree of completion of the cutting process and/or the characteristics of the tissue being cut.

Rongeur 30 of this invention is further designed so that regardless of the cutting process, the practitioner only advances/retracts the drive collar 150 and cutting tube 302. Motor 80 and drive spindle 102 remain static relative to the handpiece 34. This means that the practitioner only has to apply force needed to move the two light weight component, the drive collar 150 and the cutting tube 302. No force is needed to displace the motor 80 or drive spindle 102. This minimizes the extent to which the practitioner is required to supply large amounts of force that can induce muscle fatigue. A related feature is that should the rongeur be oriented in a position other than holding the cutting unit 240 horizontally, force does not provided to overcome the effect gravity would have on either the distal advancement or proximal retraction of the drive spindle and motor.

V. Alternative Embodiments

The above is directed to one specific version of the rongeur of this invention. Alternative versions of the rongeur may have features different from what has been described.

For example, the described handpiece 34 is designed specifically as the rongeur of this invention. In an alternative construction of this invention, the handpiece is actually a combination of a powered surgical tool designed to perform another task and a front end attachment that includes components that facilitate the simultaneous and independent powered rotation and manual advancement/retraction of the cutting implement. One such powered surgical tool that can be used form this type of handpiece is wire driver. As implied by its name, a wire driver is used to advance a wire into tissue. This type of tool has a cannulated drive shaft that is rotated or oscillated. A front end attachment with a drive spindle, drive collar, trigger and lock ring similar to those described above can be fitted to the wire driver. This would make it possible to provide the advantages of this invention without having to provide a handpiece solely designed to function as the rongeur handpiece.

Handpiece 34 is described as having a drive train that oscillates the cutting implement. This again should be understood to be exemplary and not limiting. In an alternative version of the invention, the rongeur handpiece may be designed to repeatedly rotate the attached cutting implement in successive 360° rotations about the longitudinal axis of the implement. Likewise depending on the form of the drive train, including the ability to control the motor, the handpiece may be designed to either repeatedly rotate or oscillate the rongeur.

Figure 25:
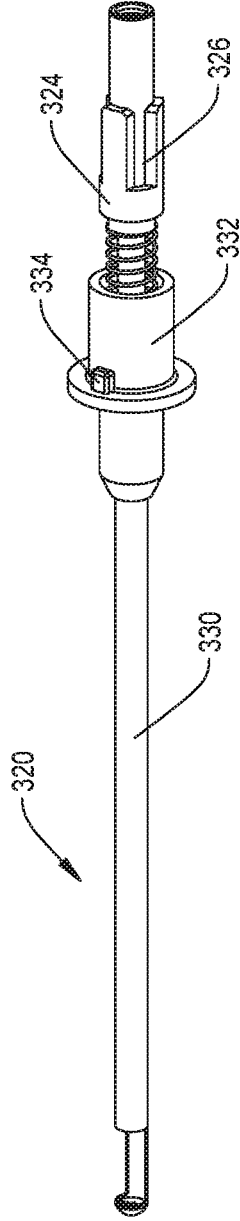
FIG. 25 is a side view of an alternative cutting unit.
Figure 25A:
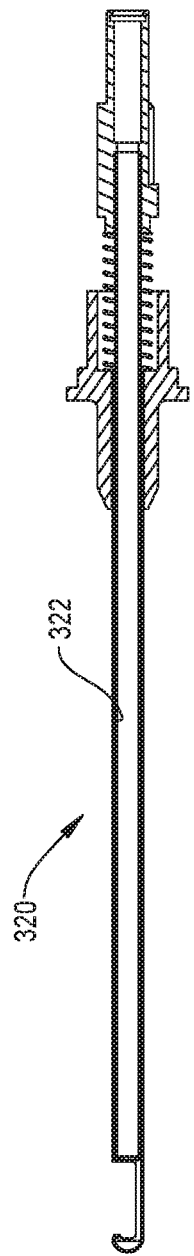
FIG. 25A is a cross sectional view of the cutting unit of FIG. 25.

The construction of features of the rongeur may also vary from what has been described. There is no requirement in all versions of the invention that the drive spindle and cutting implement have complementary non-circular surfaces that facilitate the transfer of the rotational moment of the spindle to the cutting implement. For example, in some versions of the invention, one of the drive spindle or cutting implement may have one or more pins that seat in one or more complementary slots associated with the other of the cutting implement or drive spindle. FIGS. 25 and 25A depict such an alternative cutting unit 320. Here the cutting unit has a cutting tube 322 with cutting tube hub 324. Hub 324, while being generally circular in cross section is formed with slots 326. A hub 332 is disposed over the proximal end of the outer tube 330. Hub 332 is formed with a tab 334 that seats in a complementary notch in the handpiece (not illustrated).

Figures 24A, 24B, 24C, 24D:
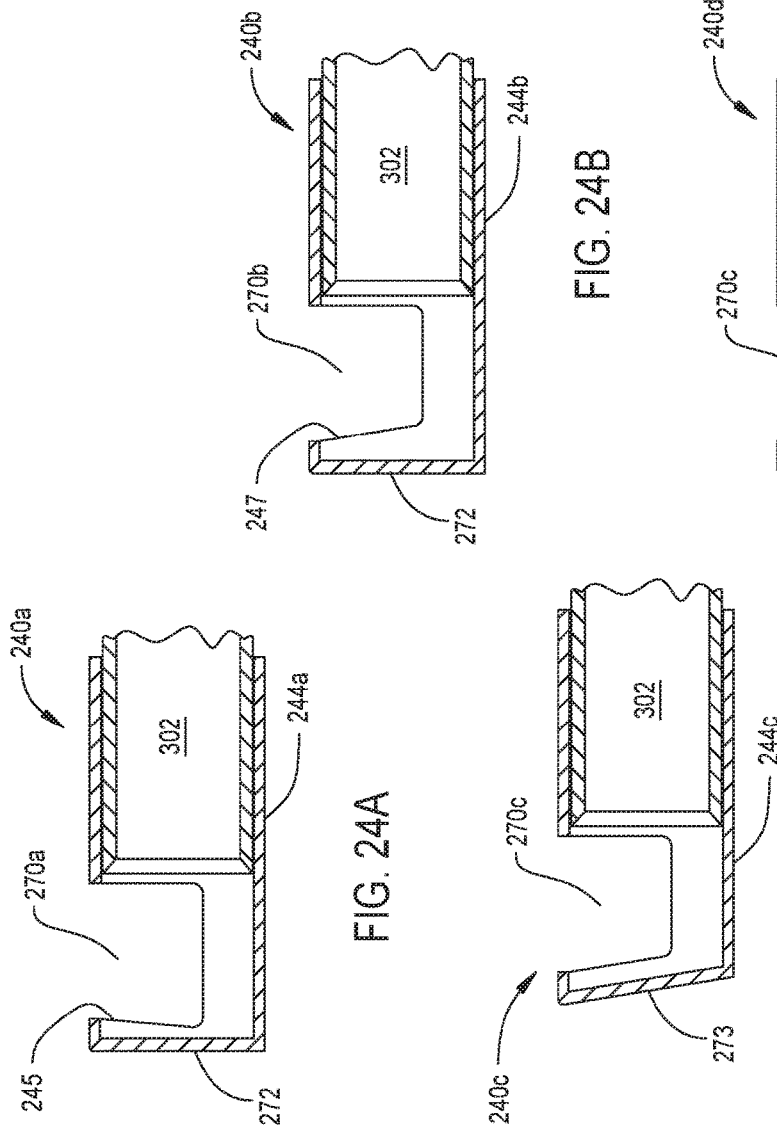
FIGS. 24A through 24D illustrate alternative shapes for the distal ends of the outer tube and cutting implement integral with the cutting unit.

FIGS. 24A through 24D, 25 and 25A illustrate alternative how the distal end portion of the outer tube of the cutting unit, including the notch formed in the tube, may have an alternative shape than the described version. FIG. 24A illustrates in cross section the distal end of a cutting unit 240a with an alternative outer tube 244a. Outer tube 244a is formed so that the tube notch 270a is defined by an edge 245 in the tube that from center of the notch extends distally forward. FIG. 24B illustrates in cross section that distal end of an alternative cutting unit 240b that includes outer tube 244b. Outer tube 244b is shaped to define a notch 270b. More specifically, the tube 244b is shaped so that an edge 247 defines the distal end of notch 279b. The tube 240b is formed so that as edge 247 extends away from the center of the notch, the edge extends proximally rearward.

The distal end of an alternative cutting unit 240c is seen in FIG. 24C. Cutting unit 240c includes an outer tube 244c and the cutting tube 302. Outer tube 244c differs from the previously described outer tubes 244, 244a and 244b in that the tube 244c is provided with face plate 273. More specifically, tube 244c is formed so that face plate 273 seats on a plane that is perpendicular to the longitudinal axis through the tube. More specifically, the tube 244a is constructed so the most distal portion of the face plate 273 is located adjacent the widest diameter portion of tube notch 270. FIG. 24D depicts an alternative cutting unit 240d. Cutting unit 240d includes the previously described outer tube 244c as well as cutting tube 303. Cutting tube 303 is substantially the same as cutting tube 302. The difference between the tube is that the cutting edge of tube 302 is on a plane perpendicular to the longitudinal axis through the cutting tube. The cutting edge of tube 303 is on a plane that is substantially parallel to the plane of the outer tube face plate 273

Likewise, the assembly for releasably holding the cutting unit 240 to the handpiece 34 need not be the described lock ring. In alternative version a ball-in-groove coupling assembly similar to that in Inventor's Assignee's U.S. Pat. No. 6,689,050, now incorporated by reference may be used to hold the outer tube to the handpiece. Still another potential locking assembly is a pin-in-slot assembly such as the one disclosed in the Inventor's Assignee's US Pat. Pub. No. 2004/0059363 also incorporated herein by reference.

Further it should be recognized that the cutting feature at the distal end of the cutting implement may not be the above described sharp circular edge. This feature may consist of a set of teeth. In some versions of the invention the cutting feature may be a bur head this is disposed at the end of the cutting tube. Examples of bur heads are disclosed in US Pat. Pub. No. US 2010/121365 now incorporated herein by reference. In these versions of the invention, proximal to where the bur head extends from the cutting tube, the cutting tube has a window. This window functions as the inlet port through which suction is drawn through the cutting tube.

In some versions of the invention the cutting unit may not include an outer hub and/or an inner hub. In versions of the invention without an outer hub the lock assembly for releasably holding the outer tube to the handpiece may be entirely within the handpiece. In versions of the invention without an inner hub the features for holding the cutting implement to the drive spindle so that the cutting implement is able to simultaneously rotate with the spindle while moving longitudinally with the spindle may be wholly built into the drive spindle. Likewise the features for longitudinally advancing/retracting the cutting implement away from/back towards the drive spindle may be completely built into the assembly that advances/retracts the cutting implement.

There is no requirement that in all versions of the invention the handpiece and cutting unit be designed to facilitate the supply of irrigating fluid to the site to which the cutting unit is applied and/or the draw of suction through the cutting implement.

The structure of the handpiece may likewise vary. There is no requirement that the handpiece always be generally pistol shaped. In some versions of the invention, the handpiece may be designed to have an elongated pencil like shape. In these and other versions of the invention, the trigger may not function as the manually actuated member that is displaced to advance and retract the cutting implement. In these alternative constructions of the invention the member that is manually actuated may be collar or tab that is slidably mounted to the handpiece. For example, if the handpiece is pencil shaped, it may be desirable to provide a tab as the manually actuated member. This way, the practitioner could hold the handpiece with his/her fingers while sliding the tab to advance and retract the cutting implement.

From the above it should be understood that the components integral with the assembly that advances/retracts the cutting implement between the proximal and distal positions of the tube may be different from what is described. There is no requirement that in all versions of the invention this assembly include a drive collar that completely circumferentially surrounds the cutting implement. In versions of the invention wherein there is a drive collar, the collar may not completely circumferentially surround the cutting implement. Likewise, there is no requirement that in all versions of the invention this drive component move over the spindle 102.

In an alternative version of the invention, this assembly may consist of a pin or a foot that is positioned to engage in a complementary opening associated with the cutting implement. This pin or foot is mounted to the handpiece to move longitudinally within the handpiece. The manually actuated control member is connected to this pin or foot to set the longitudinal positioned of the pin or foot. A benefit of this design is that it can possibly eliminate the need to provide a biasing component that normally holds the cutting implement in the proximal, retracted away, position.

Similarly, in some versions of the invention significant features that hold the outer tube static to the handpiece may be built into the tube. Thus in some versions of the invention, flexible tabs integral with the outer tube snap fit into notches integral with the handpiece to hold the outer tube in place. The tabs are manually flexed to remove the outer tube from the handpiece when it is necessary to remove the cutting unit from the handpiece.

Similarly, it should be appreciated that there is no requirement that in all versions of the invention the motor be a DC motor or even an electric motor. In some versions of the invention, the motor may be pneumatic or hydraulically driven motor. Likewise the handpiece portion of the motor may consist of the distal end components of a cable mechanism that actuates the drive spindle. In versions of the invention wherein the motor is electrically driven, the handpiece may include a battery for providing power to the motor.

In some versions of the invention, the spindle may be an integral part of the motor. Thus, when the motor is an electric motor, the spindle may be the motor rotor. Thus, there is no requirement that in all versions of the invention in which a motor is attached to the body, the motor extend along an axis that is off axis to the longitudinal axis of the spindle.

Some versions of the handpiece of this invention may be used to hold a cutting unit that does not include an outer tube.

In some versions of the invention, the spindle may not contain a through bore through which a suction can be drawn. This invention of the invention may be of use if the rongeur is intended to be used a biopsy tool that only extracts a small section of tissue.

In some versions of the invention the biasing member that normally holds the cutting implement away from the distal end of the outer tube may not be a spring that is part of the cutting unit 240. In these versions of the invention, this biasing member may extend between a static surface internal to the body 36 and the cutting tube 302.

Thus it is an object of the appended claims to cover all such variations and modifications that come within the true spirit and scope of this invention.

What is claimed is:

1. A configured to excise tissue, said rongeur for comprising:
    a cutting unit including an outer tube and a cutting implement that is slidably disposed within the outer tube, the outer tube and cutting implement each having a distal end;
    a body separate from the cutting implement;
    a mounting assembly attached to at least one of said body or the cutting unit and configured to removably mount the cutting unit to said body;
    a spindle rotatably disposed in said body, said spindle configured to engage the cutting implement so that the cutting implement rotates with the spindle and said spindle including a feature for holding the cutting implement to said spindle so that the cutting implement can move longitudinally relative to said spindle and so that when the cutting implement is moved longitudinally relative to said spindle, said spindle is able to simultaneously rotate the cutting implement with said spindle;
    a power source connected to said spindle for rotating the spindle;
    a cutting implement advancement/retraction assembly moveably attached to said body that releasably engages the cutting implement and that is configured to, upon actuation, longitudinally move the cutting implement relative to said spindle so that the distal end of the cutting implement can be extended towards and retracted away from the distal end of the outer tube of the cutting unit; and
    wherein said cutting implement comprises a cutting tube, said cutting tube configured to define a fluid communication path to draw excised tissue through said cutting tube.

2. The rongeur of claim 1, wherein said cutting implement advancement/retraction assembly includes a collar that is disposed in said body so as to be movable longitudinally in said body and is located adjacent the cutting implement so that the displacement of said collar results in said collar abutting the cutting implement and displacing the cutting implement relative to said spindle.

3. The rongeur of claim 2, wherein said collar is mounted to said body so as to move over the spindle.

4. The rongeur of claim 2, wherein said collar is shaped to circumferentially surround the cutting implement.

5. The rongeur of claim 1, wherein said cutting implement advancement/retraction assembly includes: a drive member moveably mounted in said body to abut and displace the cutting implement relative to the spindle; and an external driver mounted to and external to said body that is manually displaced and connected to said drive member for moving said drive member.

6. The rongeur of claim 5, further comprising a biasing component disposed against said drive member that holds said drive member in a position in which the cutting implement is retracted away from the distal end of outer tube.

7. The rongeur of claim 1, wherein said cutting implement advancement/retraction assembly includes a lever that is pivotally connected to the body that is pivotable to movably extend the cutting implement towards the distal end of the cutting unit.

8. The rongeur of claim 1, wherein said power source is a motor attached to said body.

9. The rongeur of claim 8, wherein said motor is attached to the body so as to extend along an axis that is not coaxial with said spindle.

10. The rongeur of claim 1, wherein said power source and said spindle are collectively configured so that the actuation of said power source causes said spindle to oscillate so the oscillation of said spindle results in the like oscillation of the cutting implement.

11. The rongeur of claim 1, further comprising:
    a first biasing member that acts against the cutting implement to hold the cutting implement away from the distal end of the outer tube; and
    a second biasing member that extends between said body and said cutting implement advancement/retraction assembly that inhibits the movement of the assembly that results in the advancement of the cutting implement towards the distal end of the outer tube.

12. The rongeur of claim 11, wherein said first biasing member extends between outer tube and cutting unit cutting implement.

13. The rongeur of claim 1, wherein said mounting assembly includes a lock ring that is rotatably mounted to the body to releasably hold the outer tube to said body.

14. The rongeur of claim 1, wherein said spindle comprises a distal bore and a proximal bore, said distal bore and said proximal bore are configured to form a through channel between a distal end and a proximal end of said spindle; and wherein said distal bore is communicably coupled to said fluid communication path defined by said cutting tube and configured to receive excised tissue from said cutting tube.

15. The rongeur of claim 14, further comprising a cap at least partially disposed in said body and positioned adjacent a proximal end of said spindle, wherein said cap comprises:

an elongated tube at least partially disposed in said proximal bore of said spindle and defining a channel through said cap to receive excised tissue from said spindle.

16. The rongeur of claim 15, wherein said cap further comprises a feature configured to receive a suction line.

17. The rongeur of claim 14, wherein said distal bore of said spindle, in cross section, exhibits a non-circular shape.

18. The rongeur of claim 1, wherein the outer tube of the cutting unit is formed with a notch proximate to said distal end of said outer tube through which tissue enters the outer tube;

wherein said cutting tube comprises a beveled surface proximate said distal end of said cutting tube which defines a cutting edge; and wherein distal to said notch, said outer tube has a face plate toward which said cutting tube is movable so that said cutting edge of said cutting tube acts against and excises tissue that extends through said notch into said outer tube.

* * * * *

UNITED STATES PATENT AND TRADEMARK OFFICE
CERTIFICATE OF CORRECTION

PATENT NO. : 10,206,702 B2  
APPLICATION NO. : 15/185199  
DATED : February 19, 2019  
INVENTOR(S) : James G. Walen Page 1 of 1

It is certified that error appears in the above-identified patent and that said Letters Patent is hereby corrected as shown below:

In the Claims

Column 17, Line 56:
Delete "A configured to excise tissue, said rongeur comprising:" and add -- A rongeur configured to excise tissue, said rongeur comprising: --

Column 19, Line 4:
Delete "member extends between outer tube and cutting unit cutting implement" and add -- member extends between outer tube and cutting implement --

Signed and Sealed this  
Sixth Day of August, 2019

Andrei Iancu  
*Director of the United States Patent and Trademark Office*